(12) United States Patent
Kagenow

(10) Patent No.: US 7,198,066 B2
(45) Date of Patent: Apr. 3, 2007

(54) DEVICE FOR SUPPORTING AND STABILISING A TUBING FOR FLUID TRANSPORT AND SUCH A TUBING

(75) Inventor: Lise Kagenow, London (GB)

(73) Assignee: Novarix Ltd., Oxford Centre for Innovation, Oxford (GB)

(*) Notice: Subject to any disclaimer, the term of this patent is extended or adjusted under 35 U.S.C. 154(b) by 0 days.

(21) Appl. No.: 10/493,372

(22) PCT Filed: Oct. 22, 2002

(86) PCT No.: PCT/DK02/00702

§ 371 (c)(1),
(2), (4) Date: Jul. 20, 2004

(87) PCT Pub. No.: WO03/035160

PCT Pub. Date: May 1, 2003

(65) Prior Publication Data

US 2005/0011568 A1   Jan. 20, 2005

(30) Foreign Application Priority Data

Oct. 23, 2001 (DK) ............................. 2001 01555
Apr. 17, 2002 (DK) ............................. 2002 00563

(51) Int. Cl.
*F16L 11/00* (2006.01)

(52) U.S. Cl. ............. 138/110; 138/106; 128/DIG. 26; 604/174; 604/177; 604/180

(58) Field of Classification Search ............... 604/174, 604/180, 177, 179, 523; 138/106, 110, DIG. 8; 128/DIG. 26
See application file for complete search history.

(56) References Cited

U.S. PATENT DOCUMENTS

| | | | | |
|---|---|---|---|---|
| 124,897 A | * | 3/1872 | Honsinger | 138/110 |
| 1,156,145 A | * | 10/1915 | Jenkins | 285/64 |
| 1,731,322 A | * | 10/1929 | Riddle | 433/96 |
| 2,147,124 A | * | 2/1939 | Litle, Jr. | 251/147 |
| 2,229,849 A | * | 1/1941 | Heidebrecht | 174/84 R |
| 2,530,812 A | * | 11/1950 | Carmer, Jr. et al. | 174/135 |

(Continued)

FOREIGN PATENT DOCUMENTS

EP   0 488 821   2/1991

(Continued)

*Primary Examiner*—James Hook
(74) *Attorney, Agent, or Firm*—Gifford, Krass, Sprinkle, Anderson & Citkowski, P.C.

(57) ABSTRACT

The present invention relates to an anti-kinking device, in particular for supporting and stabilising an infusion tubing for fluid infusion in a safety loop, comprising means for receiving and fixing the infusion tubing in connection with a catheter inserted into a superficial vein or the like and connected to an infusion container via the infusion tubing, said device being fixable to a patient in order to relieve the tension of the tubing at the point of insertion. This provides a device for flexible support of an infusion tubing to create a safety loop in a simple and flexible manner.

18 Claims, 7 Drawing Sheets

U.S. PATENT DOCUMENTS

| | | | |
|---|---|---|---|
| 2,727,512 A | 12/1955 | Muller | |
| 2,769,999 A * | 11/1956 | Sheahan | 15/327.2 |
| 3,618,613 A | 11/1971 | Schulte | |
| 3,853,148 A * | 12/1974 | De Vincent et al. | 138/110 |
| 3,942,528 A * | 3/1976 | Loeser | 604/174 |
| 4,029,103 A * | 6/1977 | McConnell | 604/179 |
| 4,151,864 A * | 5/1979 | Thurman | 138/106 |
| 4,345,616 A | 8/1982 | Terry | |
| 4,435,174 A * | 3/1984 | Redmond et al. | 604/174 |
| 4,484,914 A | 11/1984 | Brown | |
| 4,820,274 A * | 4/1989 | Choksi et al. | 604/174 |
| 4,889,168 A * | 12/1989 | Kerzich et al. | 138/103 |
| 4,897,082 A | 1/1990 | Erksine | |
| 4,976,698 A | 12/1990 | Stokely | |
| 5,147,320 A * | 9/1992 | Reynolds et al. | 604/174 |
| 5,192,273 A | 3/1993 | Bierman | |
| 5,306,245 A * | 4/1994 | Heaven | 604/523 |
| 5,314,411 A | 5/1994 | Bierman et al. | |
| 5,496,283 A * | 3/1996 | Alexander | 604/180 |
| 5,626,565 A * | 5/1997 | Landis et al. | 604/174 |
| 5,916,199 A * | 6/1999 | Miles | 604/174 |
| 6,001,081 A | 12/1999 | Collen | |
| 6,022,343 A | 2/2000 | Johnson et al. | |
| 6,129,715 A | 10/2000 | Cunningham | |
| 6,159,198 A * | 12/2000 | Gardeski et al. | 604/523 |
| 6,167,914 B1 * | 1/2001 | Koteskey | 138/110 |
| 6,273,873 B1 * | 8/2001 | Fleischer | 604/174 |
| 2002/0163183 A1 * | 11/2002 | Ooi et al. | 285/93 |
| 2003/0178086 A1 * | 9/2003 | Hu | 138/156 |

FOREIGN PATENT DOCUMENTS

| | | |
|---|---|---|
| WO | WO 89/01349 | 2/1989 |
| WO | WO 88/01877 | 3/1998 |
| WO | WO 99/56802 | 11/1999 |
| WO | WO 99/64097 | 12/1999 |

* cited by examiner

FIG - 5A
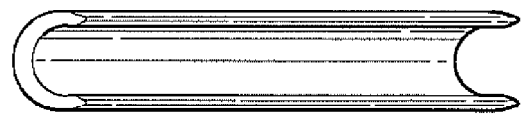
FIG - 5B
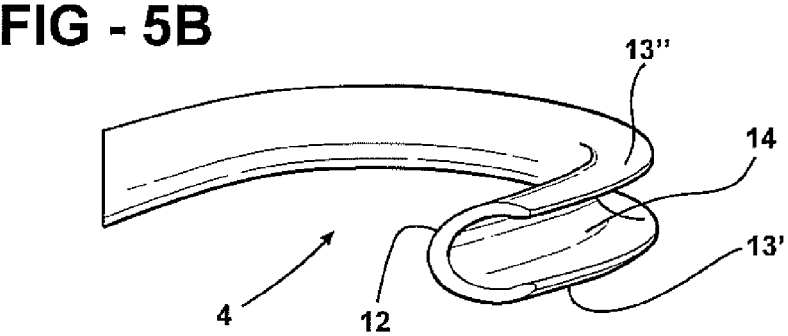
FIG - 5C
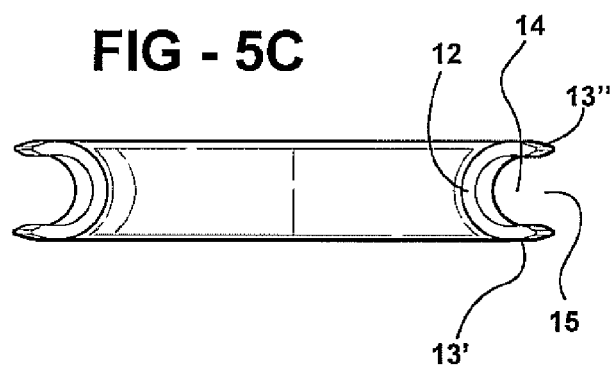
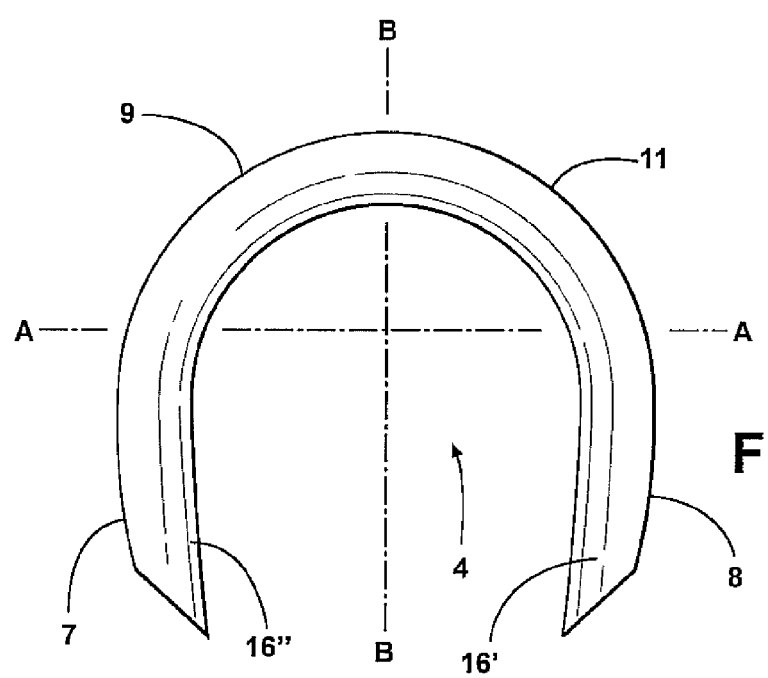
FIG - 5D

FIG - 7A
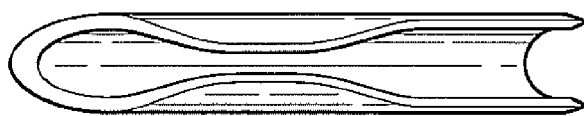
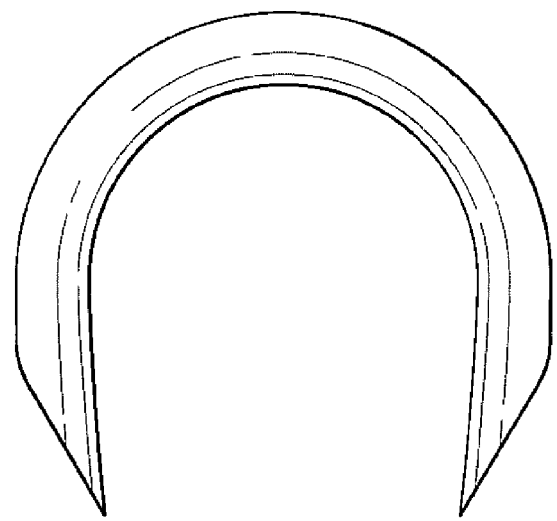
FIG - 7B
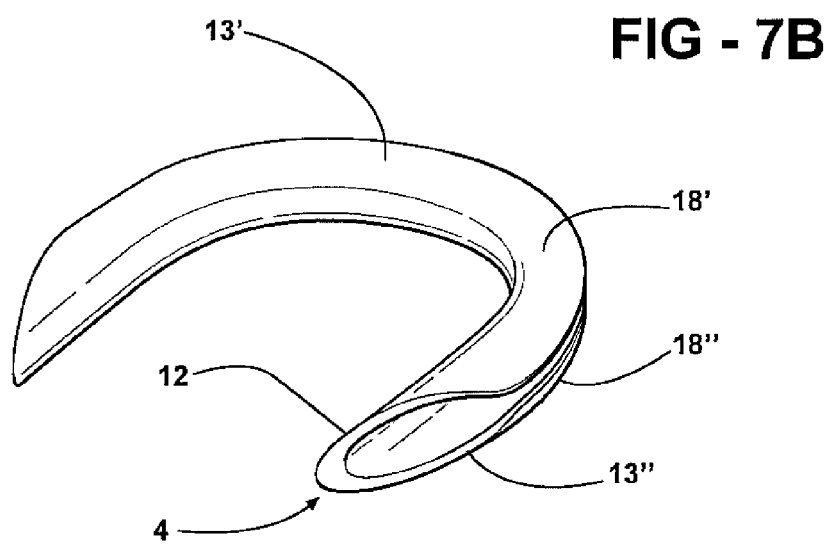
FIG - 7C

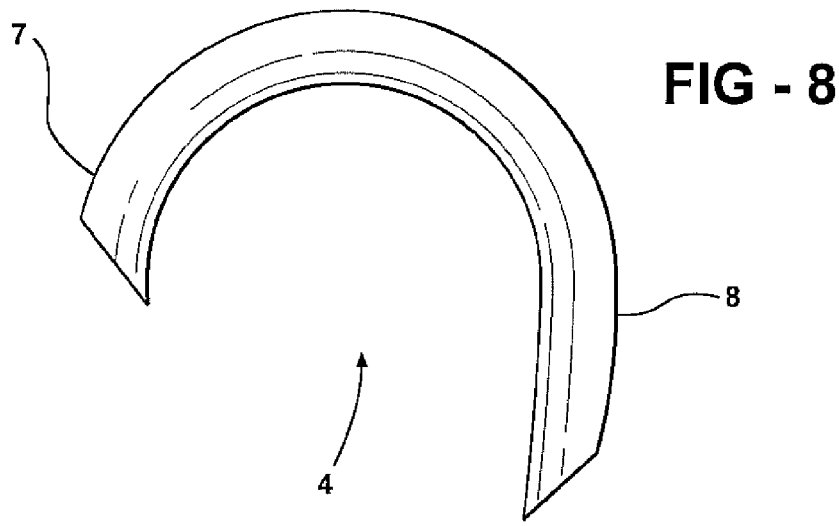
FIG - 8
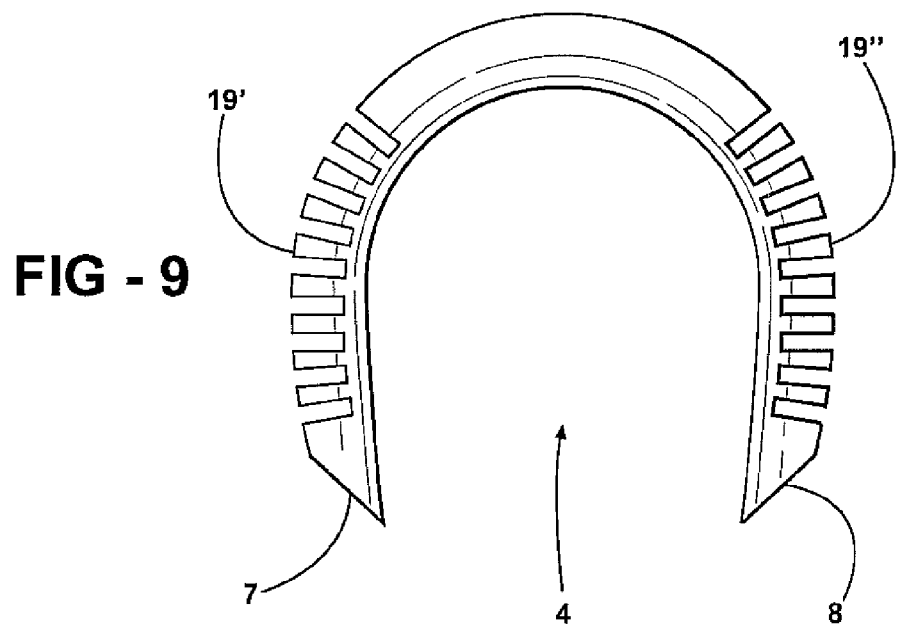
FIG - 9
FIG - 10A
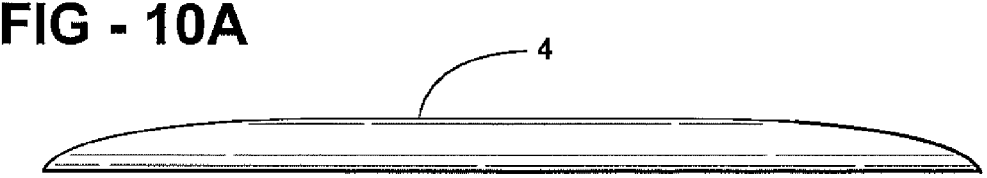

DEVICE FOR SUPPORTING AND STABILISING A TUBING FOR FLUID TRANSPORT AND SUCH A TUBING

The present invention relates to an anti-kinking device for supporting and stabilising a tubing, such as a tubing for fluid infusion.

BACKGROUND

For the intravenous administration of fluids such as blood, electrolytes, medicine, foodstuffs and the like, one normally uses a hollow needle or a catheter introduced into a superficial artery or vein and connected through a tubing to the infusion container. The tubing is normally fixed to the patient's skin with an adhesive plaster or a bandage close to the point of insertion in order to stabilise it. Because of the flexibility of the tubing, the patient's movements or weak parts of the tubing may cause the tubing to bend, thus obstructing or even stopping the infusion.

In order to obtain a continuous and optimum rate of flow of the administered infusion fluid, the rate of flow must be regularly and carefully controlled. The control of the rate of infusion is important in order to obtain optimum therapeutic results. Means for the control of flow such as catheter clamps, dropping chambers and infusion pumps are a contributing factor, but the function of these means becomes inoperative when the tubing bends. A bend of the tubing may entail a prolonged time of infusion or even a complete stop of the infusion, which has important consequences for the patient.

When administering infusion fluid to a patient, it is common to make a safety loop and fix this loop to the patient in order to prevent the weight and direction of the tubing from causing traction to the catheter introduced into a superficial vein and thus causing the catheter to be drawn out of the patient.

WO-A-99/56802 discloses a device for supporting tubing in a safety loop in which the outer body of the device is shaped as the safety loop and in which the tubing is placed along with and attached to the device. However, this device suffers from the drawback that it consists of two parts assembled around the tubing, which makes it difficult to use the device. Moreover, this device has an extra component that has to be fixed with separate plaster or a similar further component in the vicinity of the point of insertion which is already loaded with a catheter, a fixation plaster for retaining the catheter, and an assembly device for catheter and infusion tubing.

It is of crucial importance that the catheter is situated as steadily as possible in order to avoid that it settles against the vascular wall or a venous valve and thus obstructs the infusion—or that it perforates the vascular wall so that the infusion fluid enters into the surrounding tissue.

The device according to WO-A-99/56802 describes a compact support of the infusion tubing in the entire curve, but it may involve great difficulties to fix the safety loop with this device onto anatomically complicated locations, e.g. onto the back of the hand or the cubital fossa, without causing traction to or movement of the catheter. Furthermore, since the device according to WO-A-99/56802 is a compact support of the infusion tubing, the device cannot adapt to the movements of the skin of the patient and will therefore instead lead to a traction of the skin of the patient, each time the patient moves the part of the body having the device attached thereto, for example a hand.

On this background, it is the object of the present invention to provide a solution to the above-mentioned problems of the prior art to obtain a stable support of an intravenous or intra-arterial infusion tubing.

DESCRIPTION OF THE INVENTION

This object has been accomplished by means of an anti-kinking device for supporting and stabilising a tubing for fluid or air transport in a safety loop, said device comprising a proximal end and a distal end and a middle part, said proximal end being movable relative to the distal end, and said device having means for receiving and fixing the tubing, said tubing being in connection with a fluid or air recipient.

The term fluid or air recipient refers to the part receiving the fluid or air transported in the tubing. In particular the fluid recipient is a catheter inserted into a vein, an artery or the like, preferably into a superficial vein.

The tubing is preferably connected to a fluid or air dispenser, such as a fluid dispenser, such as an infusion container.

The device may be arranged on the tubing in the final position or arranged anywhere else on the tubing and then slid along the tubing the final position. In a preferred embodiment the final position is with the proximal end against any coupling means between the tubing and a catheter when the device is used for tubing connected to an intravenous or intraarterial catheter.

In the present context the term "tubing" is used synonymously with the term "line", meaning the tubing transporting liquid or fluid from a liquid or fluid dispenser to the recipient of the liquid or fluid. The device is positioned either on the outside of the tubing or integrated with the tubing wall, whereby the device cannot get access to the liquid or fluid flowing in the tubing.

In particular the anti-kinking device is for supporting and stabilising an infusion tubing for fluid infusion in a safety loop comprising means for receiving and fixing the infusion tubing in connection with a catheter inserted into a superficial vein or the like and connected with an infusion contained via the infusion tubing, said device being fixable to a patient so that the tension of the tubing is relieved at the point of insertion, and said device having a proximal end and a distal end and a middle part. The proximal end receives the infusion tubing from the point of insertion. The infusion tubing is placed into or along at least the middle part of the device and leaves it from the distal part.

The anti-kinking device is preferably only consisting of one part thereby facilitating production and handling of the device.

As described above in a preferred embodiment the anti-kinking device is suitable for use with infusion tubings for intravenous or the like infusion, whereby the device is dimensioned with respect to the diameter of the tubing. However, the anti-kinking device is equally useful for other applications wherein kinking of a tubing or a line is at risk, or for use in other medical appliances, such as for water lines for use with evaporators. Also the anti-kinking device may be used with other medical tubings, for example catheters, such as oxygen catheters and arterial catheters, for example arterial catheters for blood pressure measurements, and drain tubings, and other tubings used for transport of air, oxygen or fluid.

The same device principle may be applied to other technological fields wherein kinking is a problem, such as dimensioned for conventional water lines.

In the following the device is described in relation to infusion tubings, such as for central venous catheters as well as peripheral venous catheters, however this must not be construed as a limitation. Preferably the anti-kinking device is suitable for peripheral venous catheters.

The device is designed so that the proximal end may be moved relative to the distal end. The movements of the proximal end relative to the distal end are preferably movements from a plan parallel to the skin of the patient when the device is positioned in place on tubing attached to the skin of a patient. Thereby the device is capable of adapting to the movements of the patient, for example the movement of the hand of the patient when the device is attached to the skin on the hand. However, the proximal end and the distal end may also be movable in a direction towards each other and/or from each other. In a preferred embodiment the proximal end is capable of moving in any of the above-mentioned directions in relation to the distal end. The proximal end and the distal end are preferably parallel to each other, however the ends may deviate from parallellity, such as being constructed having a predetermined angle between the two ends. In a preferred embodiment the proximal end is connected to the distal end through the middle part only, i.e. thereby leaving the proximal end and the distal end as free ends. Therefore, the device has no parts directly connecting the proximal end with the distal end, in order to ensure the free movability between the two ends.

The middle part of the device preferably comprises the curved part of the device, wherein the curved part may be one continuous curve, as well as two or more curves spaced apart by straight section(s), and the proximal end and the distal end correspond to the straight legs of the device. In one embodiment the length of the proximal end is substantially identical to the length of the distal end, whereby the device when in use may attain the shape of a horseshoe also called a U-form. However, in another embodiment one end is longer than the other end, whereby the device when in use may attain a J-form. The length of the shortest end of the device must be large enough to ensure that the tubing when positioned with the device does not kink in the loop. In a preferred embodiment the length of each end is in the range of from 0.5 cm to 4 cm, more preferably in the range of from 1.0 cm to 3.0 cm, most preferably about 2 cm.

The curve and the length of the curved part of the device, i.e. the middle part should be dimensioned to ensure, that a loop of the tubing, said loop having a sufficient diameter in the curving, is provided when the tubing is positioned in the device. Accordingly, the length and the curve of the middle part preferably ensures that the distance between the proximal end and the distal end is at least 2.0 cm, more preferably at least 2.5 cm, most preferably at least 3.0 cm. On the other hand, the middle part of the device is preferably not too large, since the loop formed by the device on the tubing cannot be positioned in a practical and safe manner on for example a hand, if the middle part is too large.

Furthermore, when in use positioned on the tubing the device should preferably maintain the final form, such as the U-form or the J-form described above, in order to avoid kinking of the tubing positioned in the device, yet allowing the movements of the proximal end relative to the distal end as described above. This stability of the final form is either obtained by constructing the device with the final form, or by constructing the device with another form and shaping the device into the final form when it is applied to the tubing. In the latter embodiment the stability final form of the device may be ensured by thermal or the like treatment. In the latter case the device may have a tubular shape being flexible so that the device is capable of bending, for example by bending the two ends towards each other, or by bending the two ends into alignment with each other. In an alternative embodiment, the device may be designed as a flexible adhesive tape with one or more embedded, plastically mouldable elements.

To allow the movement of the proximal end relative to the distal end, the device is produced from a flexible, preferably also resilient material. Thereby movements of the proximal end relative to the distal end is allowed however in a preferred embodiment the proximal end will return to its starting position once the movement forces have been relieved, for example when the hand is turned back into its starting position.

This provides a device for flexible support of an infusion tubing to create a safety loop in a simple and flexible manner. The device according to the invention may thus be formed according to the anatomical conditions and takes up a minimum of space, and it may be an integral part of the infusion tubing or be mounted directly onto the tubing.

In one embodiment, the device is plastically mouldable. By the term "plastically mouldable" is meant a device capable of being moulded into its final form when applied to the tubing.

Intravenous infusion is routine practice within many field of medical care of both human beings and animals, and the object of the invention may thus be utilised with all types of patients, i.e. both human beings and animals.

The device is preferably designed as a longitudinal sleeve constituting a jacket to be placed around the outer portion of the infusion tubing, and having along at least a part of its entire length receiving means for maintaining the infusion tubing. Thus, it may easily be mounted on an intravenous infusion tubing. Alternatively, the jacket may be integrated in the intravenous infusion tubing, e.g. in the finished tubing system. Furthermore, the device may be provided with means for fixation, such as adhesive tape, e.g. an adhesive plaster. The jacket may be constructed having a backbone of continuous material, said backbone being capable of maintaining the final form as discussed above, and receiving means attached to the backbone. The backbone is preferably positioned along the inner curvature of the device when brought into the final form. However, the backbone may also be positioned along the outer curvature of the device having the receiving means facing the inner curvature. In yet another embodiment the backbone may exhibit a spiral shape in at least a part of the device. In another embodiment the backbone is constructed from material exhibiting discontinuities, for example as "holes" in the backbone, however this embodiment requires that the remaining material of the backbone is capable of providing the strength for keeping the final form as discussed above.

The receiving means may be positioned in order to secure the position of the tubing in the device during use. Thus, the receiving means may extend entirely along the outer curvature or inner curvature of the device or may be located at spaced apart locations along the outer curvature or inner curvature of the device either regularly or irregularly spaced apart. In one embodiment the receiving means irrespective of their form are only located on the proximal and distal ends of the device and not on the middle part of the device.

The receiving means may include adhesion means capable of adhering to the tubing when positioned in the device, or including other material capable of increasing the friction between the device and the tubing for maintaining the tubing in the device.

In one embodiment the device is formed with a backbone and the receiving means are two longitudinal side walls connected to said backbone forming a channel for the tubing. When the device comprises a channel the receiving means may comprise the two longitudinal side walls of the channel between which the tubing is frictionally engaged. The longitudinal walls may extend so that only a gap through which the tubing can be squeezed to gain access to the channel is left open, i.e. corresponding to a longitudinal slit in the device. The gap is preferably of a size marginally smaller than the external diameter of the tubing. In another embodiment the gap is substantially equally of the same size as the tubing and the longitudinal walls are provided with two or more wings extending from the walls, preferably opposing wings on the two longitudinal side walls, said wings being constructed to maintain the tubing in the device. When the longitudinal walls are provided with wings the device may be constructed with a channel capable of accomodating tubings of different diameters since it is the wings that maintain the tubing in place.

Thereby, the device has a tubular shape that is "open" so that the device may be squeezed or "clicked" in place on the tubing, and the fluid flow may take place without hindrance.

The device may be produced from any suitable material capable of providing the characteristics discussed above. In a preferred embodiment the device is produced from a plastic material, such as from a polymeric material, such as for example a polyolefin. Any suitable polymeric material may be used, such as a polymeric material selected from polyurethane, polyethylene, polypropylene, or co-polymers or mixtures thereof, or nylon or an acrylic material. In a preferred embodiment the polymeric material is selected from polyethylene or polypropylene. The device may also be produced from two or more materials, for example so that the middle part is produced from one material and one or both ends are produced from another material. An example of the latter is a middle part made from a less flexible material and the proximal end and the distal end made from a more flexible material.

The device may be produced by any suitable method, such as extrusion, moulding, and injection moulding. In particular when moulding the device into its final form, it is preferred that the device is constructed from injection moulding. Also, thereby a device made from two different materials may be produced by two-component injection moulding. It is preferred that the device is capable of being moulded in one moulding step, i.e. thereby avoiding any assembling of parts after the moulding.

Another aspect of the invention relates to an infusion tubing for fluid infusion, said infusion tubing being mountable to a catheter which is inserted into a superficial vein or the like and which is connected to an infusion container via the infusion tubing, said device being fixable to a patient for relieving the tension of the tubing at the point of insertion, where a section of the tubing is provided with a device as discussed above so that this tubing section may be maintained with a given curvature. As mentioned above, this embodiment yields an intravenous infusion tubing with an integrated device for obtaining a safety loop. The device is preferably positioned on the tubing so that it extends with one end from the connection from the tubing to the catheter in order to prevent kinking in the connection area.

It is preferred that the tubing may be observed through at least a part of the device, in order to monitor the function of the infusion and also to observe any air in the tubing. Accordingly, the device may in one embodiment be produced from a transparent material, at least in a part of the device. In another embodiment the tubing may be controlled through openings in the device.

DRAWINGS

In the following, the invention will be further described with reference to the accompanying drawings in which FIG. 1 shows an intravenous infusion tubing with a device according to the invention arranged at the back of the hand of a patient, FIG. 2 is a schematic side view of an infusion tubing with a supporting device according to the invention, FIG. 3 is a sectional view of the infusion tubing, and FIG. 4 is a perspective view of a device according to the invention.

FIGS. 5a–5d shows a device according to the invention having a U-form with a continuous backbone and two longitudinal side walls.

FIGS. 6a.6d shows a device according to the invention having a U-form with a continuous backbone and spaced apart receiving means.

FIGS. 7a–7d shows a device according to the invention having a continuous backbone and two longitudinal side walls wherein said longitudinal side walls are provided with wings.

FIGS. 8a shows a device according to the invention having J-form with a continuous backbone and two longitudinal side walls.

FIG. 9 shows a device according to the invention having a continuous backbone and two longitudinal side walls wherein a part of the material of the device is more flexible than the rest of the device.

FIGS. 10a–10d shows the device of FIG. 2 in greater detail.

DETAILED DESCRIPTION OF THE DRAWINGS

Figure 1:
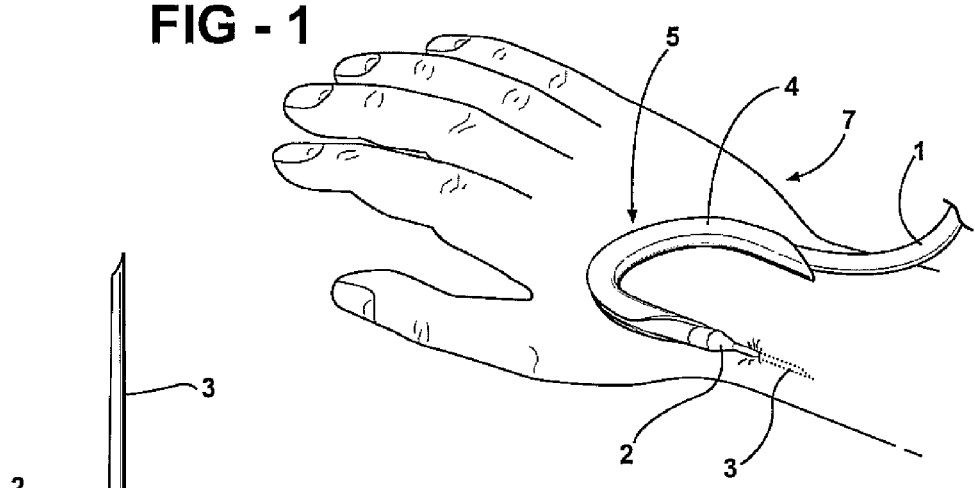

FIG. 1 shows an intravenous fluid infusion inserted in the back of the hand 7 of a patient. An infusion tubing 1 is connected to a catheter 2 which has been inserted into a superficial vein or artery and, via a safety loop 5 on the infusion tubing 1, to an infusion container (not shown). It is important that the safety loop 5 is fixed in such a manner that the catheter 2 is not pulled out of the point of insertion so that the catheter tip 3 falls out. Along the section forming the safety loop 5, the infusion tubing 1 is provided with a flexible device 4 supporting and stabilising the infusion tubing 1 in a given curvature so that it cannot break and thus cause the infusion flow to stop. This stabilising/supporting device 4 maintains its curved form. The infusion tubing 1 is mounted in the device 4, which may be fixed by means of an attached adhesive tape 6 or the like to the patient immediately after the safety loop 5. The invention contemplates the use of many other ways of fixing the device 4 or the safety loop 5 to the patient. Various types of adhesive plasters may be used according to what is suitable in the given situation, and the safety loop may be fixed by means of a bandage. The tubing 1 enters the device 4 at the proximal end 7 and is arranged in the channel followed by leaving the device 4 at the distal end 8.

The device 4 is preferably made from a material providing the characteristics of the device as discussed above.

Figure 2:
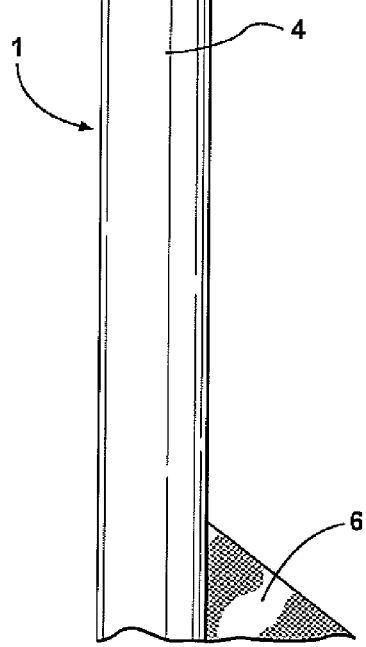
Figure 3:
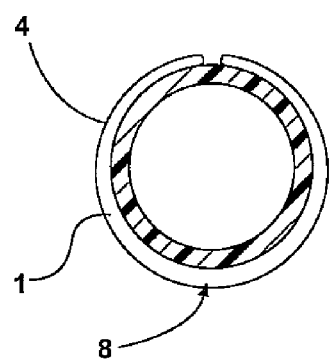
Figure 4:
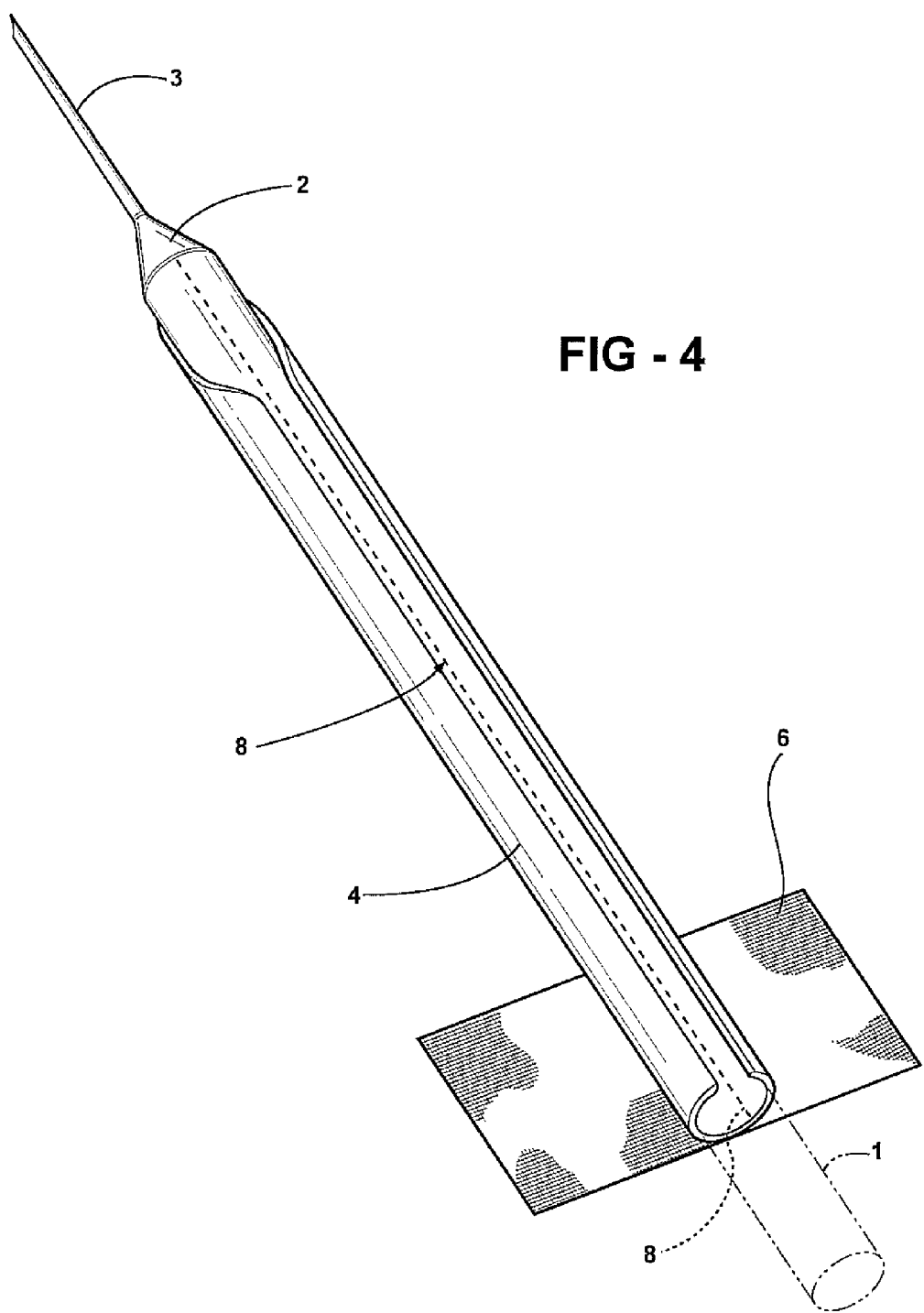
Figure 6A:
Figure 6B:
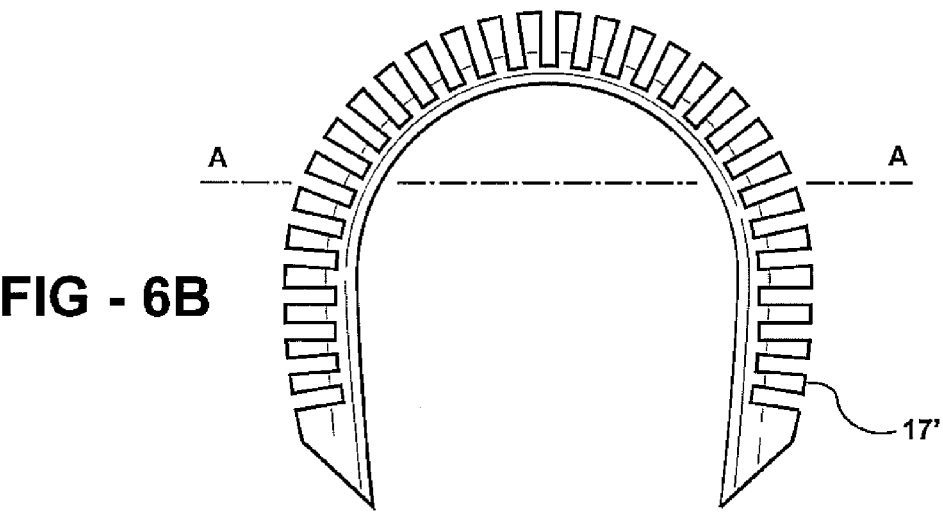
Figure 6C:
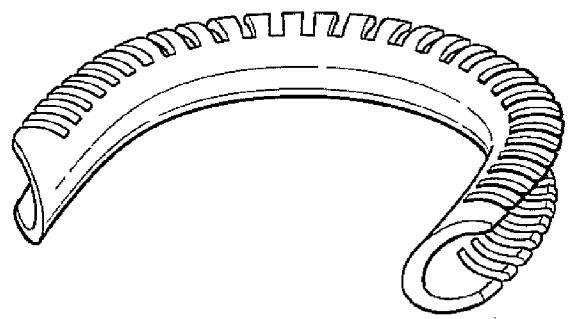
Figure 6D:
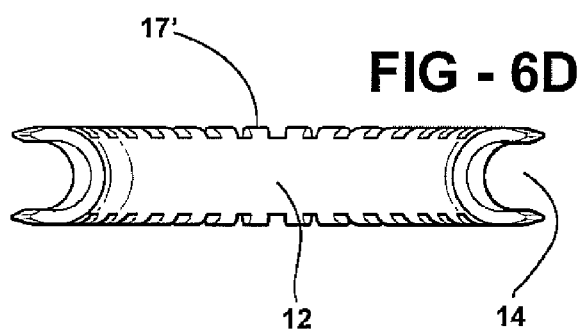
Figure 10B:
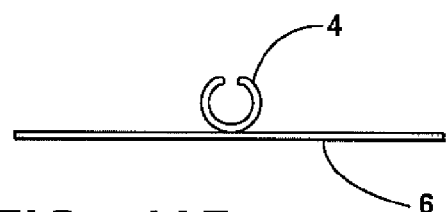
Figure 10C:
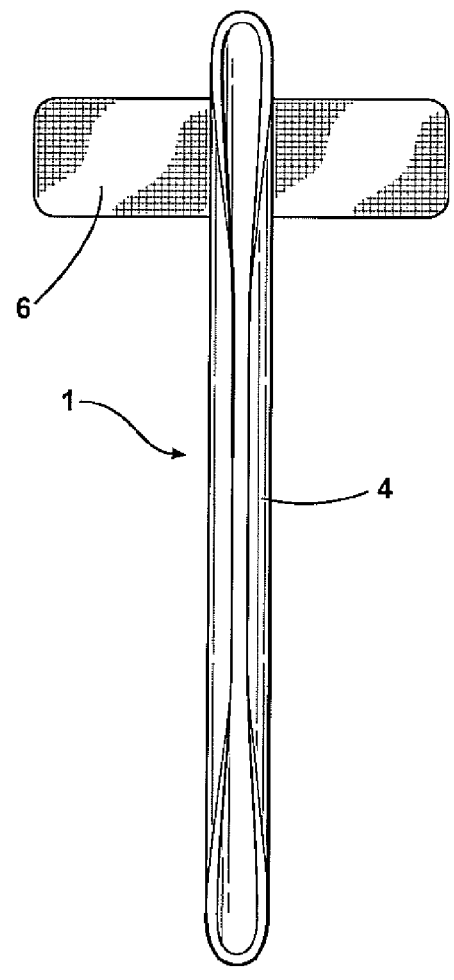
Figure 10D:
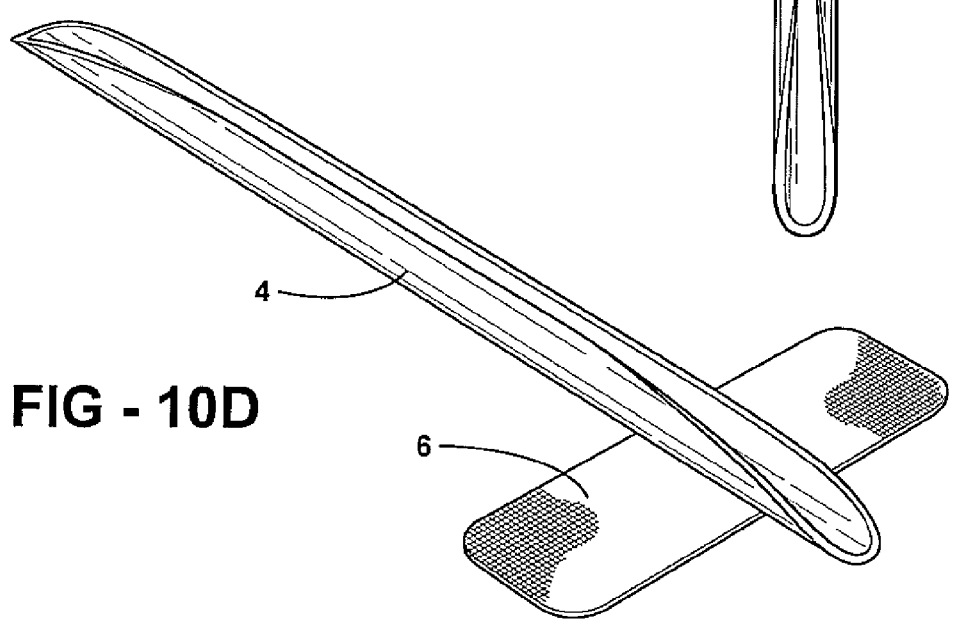

In FIGS. 2–4, the device 4 is shown in detail. The device 4 is designed as a sleeve that is placed around the infusion tubing 1. Said sleeve 4 or jacket may be "clicked" around the tubing 1 or may be attached afterwards in another manner, or it may be made as an integral part of the infusion tubing 1. The sleeve 4 is substantially tubular with an axial opening so that the sleeve 4 may be rolled on or otherwise placed around the infusion tubing 1. The sleeve 4 is made of a polymeric material, preferably a biologically inactive material which is transparent or at least translucent. The polymeric material may be plastically mouldable in itself.

The sleeve may then be made of an elastic, very flexible polymer so that the sleeve 4 becomes very easily mouldable and takes up a minimum of space. The sleeve 4 is easy to form in accordance with the anatomical conditions at the point of insertion. Thus, the infusion tubing 1 and the safety loop 5 may be securely fastened in a simple and efficient manner as the sleeve 4 can ensure that the tubing, in the entire course of the safety loop, is stabilised in a suitable form with respect to the anatomical conditions at the point of infusion.

In FIG. 5a the device 4 having a U-form is shown in greater detail in a top view. The device 4 has a proximal end 7 and a distal end 8 connected through a middle part 9. The proximal end 7 is movable in relation to the distal end 8. Each of the proximal end 7 and the distal end 8 are provided with a tapered end 13' and 13" having an angle A. The tapering of the end allows an easy appliance of the device to the tubing, and secures a stabilised position of the device against a catheter coupled to the tubing. The device 4 having an curved form exhibits an inner curvature 10 and an outer curvature 11. As may be seen from FIG. 5b the device 4 is constructed with a continuous backbone 12 and two longitudinal walls 13' and 13", said backbone 12 and longitudinal walls 13' and 13" defining a channel 14 for receiving a tubing. FIG. 5c shows a cross section of the device 4 through line A—A, through which it is apparent that the gap 15 between the outer edge of the longitudinal walls 13' and 13" is smaller than the diameter in the channel 14 defined by the backbone 12 and the two longitudinal walls 13' and 13". FIG. 5d shows a side view of the device 4.

In FIG. 6a to FIG. 6d, a device as described above with respect to FIG. 5 is shown with the exception that the continuous wall of FIG. 5 has been replaced by spaced apart receiving means 17 connected to the backbone 12. A channel 14 is defined by the backbone 12 and the spaced apart receiving means 17.

In FIG. 7 another embodiment of the device shown in FIG. 5 is shown. The device 4 has longitudinal walls 13', 13" connected to the backbone 12. Opposing each other two wings 18', 18" are extending from a respective longitudinal wall, said wings 18', 18" capable of maintaining a tubing when positioned in the device 4.

In FIG. 8 yet another embodiment of the device 4 shown in FIG. 5 is shown. The device 4 in FIG. 8 has a J form, whereby the proximal end 7 is shorter than the distal end 8.

In FIG. 9a device 4 having a U form is shown. Two parts 19', 19" of the device 4 are made from a more flexible material that the rest of the device 4. Thereby the movability of the proximal end 7 relative to the distal end 8 is facilitated.

In FIG. 10a–d the device of FIG. 2 is shown in greater detail.

The invention has been described above with reference to a working example. However, it should be understood that many variations and equivalent solutions can be made according to the invention disclosed in the attached claims.

The invention claimed is:

1. An anti-kinking device for supporting and stabilising a tubing for fluid or air transport in a safety loop, wherein the tubing is a medical tubing, said device comprising a proximal part and a distal part and a middle part, wherein the proximal part is connected to the distal part through the middle part only, and the middle part comprises a curved part, and wherein said device has a backbone, said backbone being capable of maintaining the final shape of the device, and said backbone having attached means for receiving and fixing the tubing along said backbone, when said tubing is in connection with a fluid or air recipient, and said means for receiving and fixing the tubing has an opening opposite the backbone, so that the device may be mounted to the tubing by squeezing the tubing through the opening, the opening having a size allowing a tubing section positioned in the device to be observed, said means for receiving and fixing the tubing further having projecting means projecting into the opening thereby narrowing the opening at the position of the projecting means and wherein the proximal part and/or the distal part has a tapered end, said device being fixable to a patient in order to relieve the tension of the tubing at the point of insertion.

2. The device according to claim 1, wherein the tubing is an infusion tubing.

3. The device according to claim 1, wherein the fluid recipient is a catheter inserted into a superficial vein or the like.

4. The device according to claim 1, wherein the tubing is connected to a fluid or air dispenser.

5. The device according to claim 1, wherein the device has a U form or a J form as its final form when applied to the tubing.

6. The stabilising device according to claim 1, in which the device has a backbone of continuous material and receiving means attached to the backbone.

7. The stabilising device according to claim 1, in which the device has a backbone of material with holes.

8. The stabilising device according to claim 1, in which the receiving means are located spaced apart.

9. The stabilising device according to claim 1, in which the device is designed as a longitudinal sleeve constituting a jacket to be placed around the outer portion of the tubing and which, along its entire length, has receiving means for maintaining the tubing in place.

10. The stabilising device according to claim 9, in which the sleeve is made of a polymeric material with an embedded core of plastically mouldable material.

11. The stabilising device according to claim 1, in which the device is integrated in the tubing.

12. The stabilising device according to claim 1, in which the device is provided with means for fixation of the device to a patient.

13. An infusion tubing for fluid infusion, in which the infusion tubing may be mounted to a catheter which is inserted into a superficial vein or the like and which is connected to an infusion container via the infusion tubing, said device being fixable to a patient in order to relieve the tension of the tubing at the point of insertion, said infusion tubing being characterised in that a section of the tubing is provided with the device of claim 1, so that this section of the tubing may be maintained with a given curvature.

14. The stabilizing device of claim 1, wherein the receiving means are two longitudinal sidewalls connected to said backbone and forming a channel for the tubing.

15. The stabilizing device of claim 1, wherein the means for receiving and fixing the tubing have opposing projecting means projecting into the opening thereby narrowing the opening at the position of the projecting means.

16. A method for supporting and stabilising a tubing for fluid or air transport in a safety loop, wherein the tubing is an infusion tubing or a medical catheter or drain, said method comprising:

providing an anti-kinking device in mechanical association with said tubing, said device comprising a proximal part and a distal part and a middle part, wherein said device has a backbone, said backbone being capable of maintaining the final shape of the device, and said backbone having attached thereto means for receiving and fixing the tubing along said backbone when said tubing is in connection with a fluid or air recipient, and said means for receiving and fixing the tubing has an opening opposite the backbone, said means for receiving and fixing the tubing further having projecting means projecting into the opening thereby narrowing the opening at the position of the projecting means and said proximal part and/or distal part has a tapered end;

mounting the device to the tubing by entering the tubing through the opening of the means for receiving and fixing the tubing; and affixing said device to a patient in order to relieve the tension of the tubing at the point of insertion.

17. An anti-kinking device for supporting and stabilizing a tubing for fluid or air transport in a safety loop, wherein the tubing is a medical tubing, said device comprising a proximal part and a distal part and a middle part, wherein the proximal part is connected to the distal part through the middle part only, and the middle part comprises a curved part, and wherein said device has a backbone, said backbone being capable of maintaining the final shape of the device, and said backbone having attached means for receiving and fixing the tubing along said backbone, when said tubing is in connection with a fluid or air recipient, and said means for receiving and fixing the tubing has an opening opposite the backbone, so that the device may be mounted to the tubing by squeezing the tubing through the opening, the opening having a size allowing a tubing section positioned in the device to be observed, wherein the proximal part and/or the distal part has a tapered end, and wherein said device is fixable to a patient in order to relieve the tension of the tubing at the point of insertion.

18. An anti-kinking device for supporting and stabilising a tubing for fluid or air transport in a safety loop, wherein the tubing is a medical tubing, said device comprising a proximal part and a distal part and a middle part, wherein the proximal part is connected to the distal part through the middle part only, and the middle part comprises a curved part, and wherein said device has a backbone, said backbone being capable of maintaining the final shape of the device, and said backbone having attached means for receiving and fixing the tubing along said backbone, when said tubing is in connection with a fluid or air recipient, and said means for receiving and fixing the tubing has an opening opposite the backbone, so that the device may be mounted to the tubing by squeezing the tubing through the opening, the opening having a size allowing a tubing section positioned in the device to be observed, said means for receiving and fixing the tubing further having a pair of opposed projecting wings projecting into the opening, said wings having a length which is less than the length of the opening, said wings being disposed and operative to narrow only a portion of the length of the opening, and wherein the proximal part and/or the distal part has a tapered end.

* * * * *